US009392824B1

(12) United States Patent
Leschinsky (10) Patent No.: US 9,392,824 B1
(45) Date of Patent: Jul. 19, 2016

(54) SELF-DISINFECTING PROTECTIVE GARMENT

(71) Applicant: Mark Daniel Leschinsky, Mahwah, NJ (US)

(72) Inventor: Mark Daniel Leschinsky, Mahwah, NJ (US)

( * ) Notice: Subject to any disclaimer, the term of this patent is extended or adjusted under 35 U.S.C. 154(b) by 6 days.

(21) Appl. No.: 14/583,339

(22) Filed: Dec. 26, 2014

(51) Int. Cl.
*A41D 13/00* (2006.01)
*A41D 27/20* (2006.01)
*A41D 13/12* (2006.01)
*A61L 2/18* (2006.01)

(52) U.S. Cl.
CPC ........ *A41D 13/0012* (2013.01); *A41D 13/1209* (2013.01); *A41D 27/20* (2013.01); *A61L 2/18* (2013.01); *A61L 2/186* (2013.01)

(58) Field of Classification Search
CPC .... A62B 17/001; A62B 17/00; A62B 17/006; A62B 17/005; A62B 13/00; A62B 13/0012; A62B 13/0155; A62B 13/0156; A62B 13/12; A62B 2400/14; A62D 5/00; G21F 3/02; A41D 13/02; A41D 13/0012; A41D 13/1209; A41D 27/20; A61L 2/18; A61L 2/186
USPC .......................... 2/457, 456; 588/300; 128/917
See application file for complete search history.

(56) References Cited

U.S. PATENT DOCUMENTS

| 2,761,515 | A | * | 9/1956 | Feild, Jr. | ............... | A62B 17/003 169/45 |
| 3,911,501 | A | * | 10/1975 | Seltzer | ............... | A41D 19/0058 2/163 |
| 4,062,079 | A | | 12/1977 | Potter | | |
| 4,446,860 | A | * | 5/1984 | Gutnick | .................... | A61F 6/08 128/844 |
| 4,775,372 | A | * | 10/1988 | Wilberg | ................. | A45D 34/04 401/6 |
| 4,853,978 | A | * | 8/1989 | Stockum | ................. | A61L 31/10 2/167 |
| 5,045,341 | A | * | 9/1991 | Shlenker | ................... | A61F 6/04 128/844 |
| 5,120,304 | A | * | 6/1992 | Sasaki | ................. | A61M 1/0084 2/159 |
| 5,146,625 | A | | 9/1992 | Steele | | |
| 5,169,251 | A | * | 12/1992 | Davis | ................. | A41D 19/0079 401/132 |
| 5,483,697 | A | * | 1/1996 | Fuchs | ................ | A41D 19/0058 128/844 |

(Continued)

FOREIGN PATENT DOCUMENTS

| GB | WO 2013023685 A1 | * | 2/2013 | ............... A46B 5/04 |
| WO | 2011063261 | | 5/2011 | |

*Primary Examiner* — Anna Kinsaul
*Assistant Examiner* — Griffin Hall
(74) *Attorney, Agent, or Firm* — Boris Leschinsky (57) ABSTRACT

A self-disinfecting personal protective garment comprises a plurality of pockets covered by a porous external layer. Each pocket contains (or can be filled with) a disinfecting solution. Applying compression to the flexible chamber of the pocket (such as by inflation of adjacent inflatable chambers) causes pressurization of the disinfecting solution and forces the solution to flow from the pockets across and through the porous external layer and ultimately to spread over the external surface of the protective garment—so as to eradicate the pathogens on the surface and disinfect the protective garment. Also described is a conversion kit configured to add a self-disinfecting feature to a conventional protective garment. The protective garment of the invention may be used by healthcare workers treating Ebola patients or patients with other highly contagious infections—to extend the time of garment usage, simplify garment removal procedure and increase their personal safety.

12 Claims, 7 Drawing Sheets

(56) References Cited

U.S. PATENT DOCUMENTS

| | | | |
|---|---|---|---|
| 5,603,118 A * | 2/1997 | Solomon | A41D 19/01523 2/160 |
| 5,679,399 A * | 10/1997 | Shlenker | A01N 25/10 128/844 |
| 5,755,110 A | 5/1998 | Silvas | |
| 5,846,063 A * | 12/1998 | Lakic | A41D 19/001 2/413 |
| 5,867,829 A * | 2/1999 | Hegoas | A01K 13/003 119/605 |
| 6,134,714 A | 10/2000 | Uglene | |
| 6,257,785 B1 * | 7/2001 | Otten | A45D 40/26 401/261 |
| 7,179,007 B2 * | 2/2007 | Wong | A01N 25/34 401/201 |
| 7,904,969 B2 * | 3/2011 | Greenfield | A41D 19/002 2/159 |
| 2003/0021903 A1 * | 1/2003 | Shlenker | A01N 25/10 427/385.5 |
| 2005/0045178 A1 | 3/2005 | Tang | |
| 2009/0158496 A1 * | 6/2009 | Roeckl | A41D 19/01535 2/161.1 |
| 2011/0022137 A1 | 1/2011 | Ennis-Thomas | |
| 2011/0258755 A1 * | 10/2011 | Arfi | A47L 13/18 2/161.6 |

* cited by examiner

SELF-DISINFECTING PROTECTIVE GARMENT

BACKGROUND OF THE INVENTION

The present invention relates generally to personal protective apparel. More particularly, the invention describes a self-disinfecting protective garment, which can be used by healthcare worker when treating patients with communicable diseases.

Medical professionals frequently interact with patients who have communicable diseases. When treating such patients, the medical professional must take care not to become infected or ill due to the microorganisms or pathogens related to the disease. This is frequently accomplished by donning a medical gown and gloves. If the pathogen is particularly aggressive or life-threatening, additional protective equipment may be used such as hazmat suites, coveralls, masks, head covers, aprons, etc, cumulatively referred hereto as "protective garments".

Currently unfolding Ebola crisis in West Africa is a vivid and unfortunate example of the inadequacy of current pathogen control protective garments. World Health Organization reports as of November 2014 that as many as 500 plus healthcare workers had contracted the disease while treating Ebola patients, and as many as 300 of them died. This clearly calls for a better way to provide personal protection for those healthcare workers who risk their own lives when treating others.

Beyond the Ebola crisis, various other aggressive infections and drug-resistant pathogens represent a significant public health problem, which can affect individuals at work, at home, and even in the hospital. SARS, Methicillin-Resistant Staphylococcus Aureus (MRSA), Vancomycin-Resistant Staphylococcus Aureus (VRSA), *Clostridium difficile* (*C. difficile*), influenza and other pathogens are currently circumventing our traditional approaches to pathogen control, and challenging our capacity to innovate new technical solutions.

A further area of use of personal protective garments is when dealing with chemical, radiological, or biological warfare. Care for victims, general clean-up and other action necessary in case of a chemical, nuclear, or biological attack necessitates protecting of personnel from exposure to harmful compounds, particulate or pathogens.

Existing disposable protective garments have a number of serious limitations. First of all, they have limited time of use. It is recommended to change the protective garment after only 30-60 minutes of using thereof, otherwise protection of the healthcare worker may be compromised. Such frequent exchange of protective garments increases the chance of contamination by frequent handling of soiled garments, as well as increases the cost of treating patients. There is a need for a novel protective garment with extended time of use.

Secondly, donning and removal of the protective garment is a complicated procedure requiring extensive training. Two people are frequently required to properly remove a protective garment from one person. A simple misstep by either one of them may also cause inadvertent contamination and expose that healthcare worker to the pathogen. There is a need for a novel protective garment which simplifies removal process and minimizes the risk of infection while removing and discarding the garment.

Another limitation of the current protective garments is that it gets to be very hot inside for the healthcare worker who wears the garment. This is especially true in conditions of a typical Africa field hospital where most of the recent Ebola patients are being treated. Uncomfortable conditions may increase the risk of making a mistake while treating patients and the risk of exposure to the virus. There is a need for a novel protective garment that allows active cooling of the inside thereof and make it more comfortable for the healthcare worker who wears it.

Finally, there is a risk of cross-contamination by the healthcare worker of the next patient if the previous patient was indeed infected with the virus and the doctor for some reason did not change the protective garment between the patients. Efforts to avoid cross-contamination could be much more successful if healthcare workers could wear gloves, gowns, and/or other protective garments, which were self-disinfecting, and therefore did not need to be changed as often as standard protective garments, and/or could continue to provide protection against cross-contamination even if a busy doctor or nurse, for example, occasionally forgot to change his or her gloves between patients.

A number of self-decontaminating fabrics are currently on the market, utilizing copper, silver, or hydantoin-attached chloramine. However, for these fabrics the 3-log kill rates for vegetative pathogens are in the range of 1-24 hours, and many, if not most, of these current designs have little or no effect on pathogens like the Ebola virus. Therefore, while these fabrics may be useful for other purposes, they are not effective for the purposes outlined above.

What is needed, therefore, is a self-disinfecting protective garment such as a personal protective suit that provides persistent protection against both cross-contamination and user contamination, having an extended usage time and sufficiently high pathogen kill rate for life-threatening viruses such as the Ebola virus.

SUMMARY OF THE INVENTION

Accordingly, it is an object of the present invention to overcome these and other drawbacks of the prior art by providing a novel self-disinfecting protective garment capable of providing extended time of use.

It is another object of the present invention to provide a novel self-disinfecting protective garment with simplified donning and removal procedure so as to minimize the risk of user contamination while performing these steps.

It is a further object of the present invention to provide a novel self-disinfecting protective garment allowing removal by the user himself and not requiring assistance of another person.

It is yet a further object of the present invention to provide a novel self-disinfecting protective garment with visual indication of disinfection so as to assure complete disinfection of desired areas or the entire protective garment.

It is yet another object of the invention to provide a novel self-disinfecting protective garment capable of active cooling of the interior thereof during use.

Finally, it is an objective of the invention to provide a conversion kit to add a self-disinfecting feature to a conventional personal protective garment.

The new protective garment of the present invention comprises a plurality of pockets, each pocket in turn comprising a flexible impermeable chamber covered by and sealed along an edge thereof with a flexible porous external layer. This porous external layer may form a part of an external surface of the protective garment by being attached to or incorporated with the garment fabric. Importantly, each pocket may contain or can be filled with a disinfecting solution to be placed within the flexible chamber thereof. Applying compression to the flexible chamber of the pocket causes pressurization of the disinfecting solution and forces this solution to flow from the pocket across and through the porous external layer, and ultimately to spread over the external surface of the protective garment—so as to destroy the pathogens on the surface and disinfect the protective garment.

Compression of the flexible chambers may be applied manually (by pressing or rubbing a hand or another object against the external surface of the protective garment) or by air pressure applied to a plurality of inflatable chambers positioned inside or in close contact with the flexible chambers behind the disinfecting solution.

Various additives may be used in conjunction with the disinfecting solution. One example of a suitable additive may be a coloring agent selected to allow the user to observe how the disinfecting solution flows over the external surface of the protective garment—so as assure proper coverage of the garment surface. Another example of a useful additive may be an evaporating solution to promote active cooling of the garment's surface upon enhanced evaporation of the disinfecting solution. A further additive may include a thickener or a thinner of the disinfecting solution to assure its proper viscosity and prevent premature leakage from the flexible chambers across the pores of the porous external layer.

In addition to providing a garment covered at least partially by the pockets containing the disinfecting solution, the present invention describes a conversion kit comprising a plurality of pockets containing the disinfecting solution—such pockets may be applied to a conventional personal protective garment with an adhesive layer to add a self-disinfecting feature thereto.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 1:
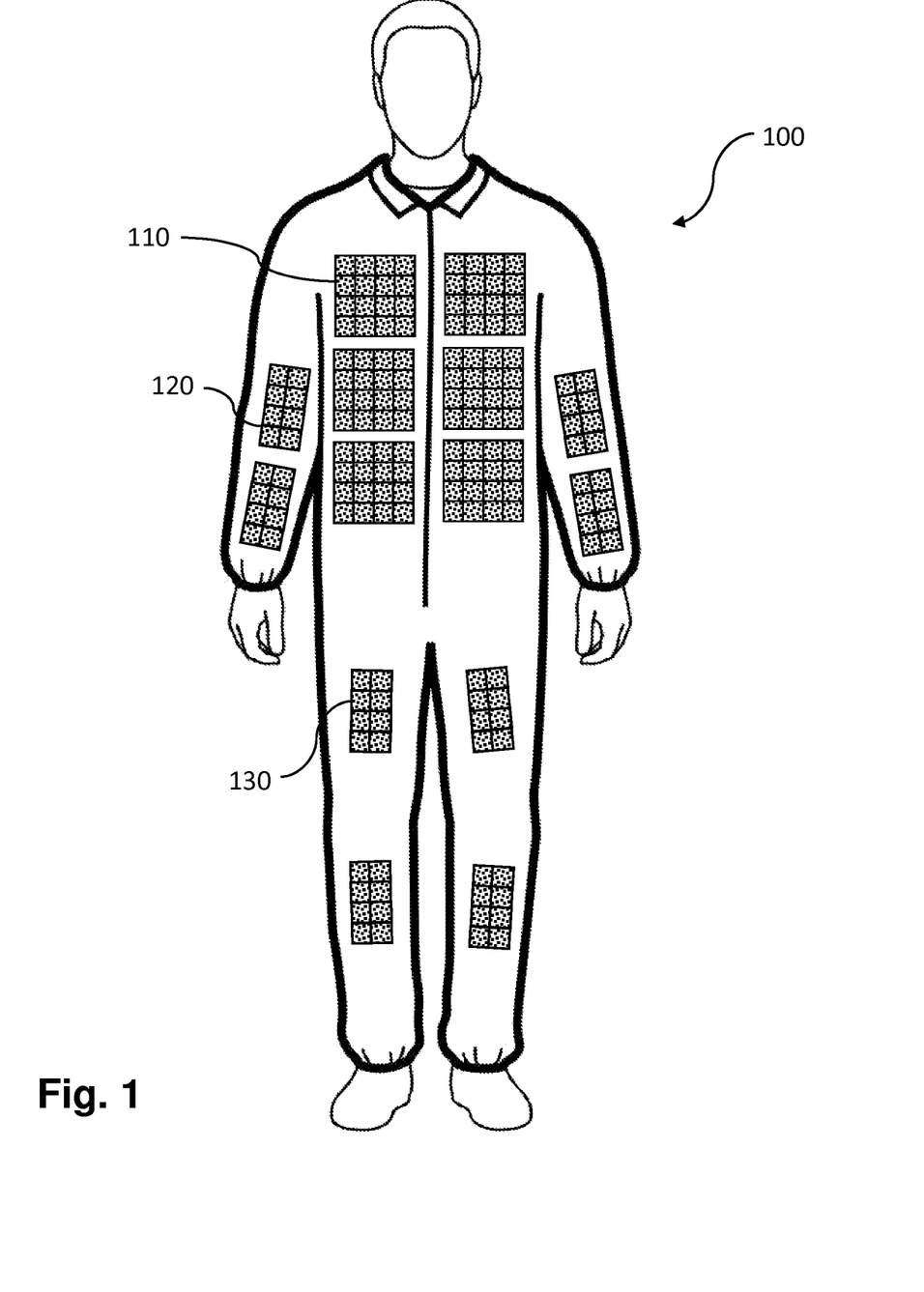
FIG. 1 is a front view of the protective garment of the invention, the protective garment shown having arm sleeve, leg, and chest areas configured to cover a wearer.

FIG. 1 illustrates the general concept of the protective garment of the present invention. A protective suit or garment 100 may include one or more pockets or pocket clusters 110, 120, or 130, these pockets are configured to contain (when prefilled with) or to be filled with a disinfecting solution. Compression of the pockets may be used to cause the disinfecting solution to flow to the external surface of the protective garment 100 and disinfect thereof.

One or more pocket clusters 110, 120, or 130 may be located on the protective garment 100 of the invention. In embodiments, such clusters may be predominantly positioned in areas of particular interest, such as:

(i) on areas that are more likely to be contaminated when the protective garment is in use, for example the front chest area as shown by pocket clusters 110;

(ii) areas that are more likely to be handled and touched during removal of the garment, such as sleeve pocket clusters 120 or leg pocket clusters 130;

(iii) areas that may be located above these areas (i) and (ii) so that when released, the disinfecting solution may flow down the protective garment 100 towards the areas of interest.

In other embodiments, the entire protective garment 100 may be covered with pockets containing the disinfecting solution.

Figure 2:
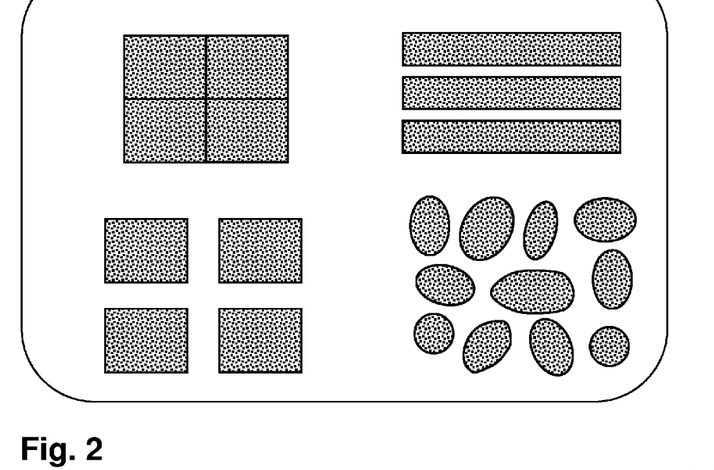
FIG. 2 illustrates various shapes of pockets filled with the disinfecting solution.

Each pocket cluster 110, 120, or 130 may contain one or a plurality of individual pockets. Such pockets may be bordering each other as seen on the upper left panel in FIG. 2—or they may be spaced apart but still be adjacent to each other as seen on the lower left panel in FIG. 2. The shape of each pocket may be rectangular, square, triangular, round, oval, or any other suitable shape as seen in FIG. 2. In other embodiments, these pockets may be made in the shape of parallel strips seen on the top right panel in FIG. 2. Such strips may be positioned and oriented horizontally—otherwise the disinfecting solution may pool down one end of the pocket and prevent its even distribution over the external surface of the protective garment 100 when flowing out of the pocket.

The size and volume of each pocket may be selected to contain a sufficient volume of the disinfecting solution for performing the disinfecting procedure at least one time. In embodiments, the width of each pocket may be in the range from about ½ of an inch to about 50 inch. In embodiments, the width of each pocket may be about ½ of an inch, ¾ of an inch, 1 inch, 1.5 inch, 2 inches, 3 inches, 4 inches, 5 inches, 10 inches, 15 inches, 20 inches, 25 inches, 30 inches, 40 inches, 50 inches or any other size as the present invention is not limited in this regard. The height of each pocket may be in the range from about ½ of an inch to about 3 inches. In embodiments, the height of each pocket may be about ½ of an inch, ¾ of an inch, 1 inch, 1.5 inch, 2 inches, 2.5 inches, 3 inches or any other size inbetween. Extending the height further may cause unwanted pooling of the disinfecting solution towards the bottom of the pocket. The term "about" is used herein and throughout the specification to describe a plus or minus variation of 30% of the cited parameter.

The internal volume of each pocket may vary from about ½ ml to about 50 ml. In embodiments, the internal volume of the pocket may be ½ ml, 1 ml, 2 ml, 3 ml, 4 ml, 5 ml, 7 ml, 10 ml, 15 ml, 20 ml, 25 ml, 30 ml, 40 ml, 50 ml or any other volume inbetween. Larger size pockets may make the protective garment 100 too heavy when filled with the disinfecting solution.

In embodiments, pockets may be sized and shaped to be the same or individually sized and shaped to cover and fit over the particular area of interest in an optimal way depending on the size and shape of this area. Each pocket 200 may comprise a flexible impermeable chamber 210 covered with and sealed along its outer peripheral edge 212 with a porous external layer 220 as seen in a cross-sectional illustration in FIG. 3a. The pocket 200 may be filled at some time prior to, during or after the use of the protective garment 100 with the disinfecting solution 250 selected to eradicate the pathogen upon coming in contact therewith as described in greater detail below.

Figure 3A:
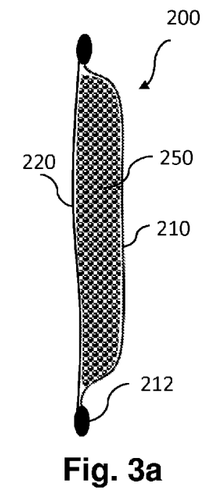
FIGS. 3a, 3b, 3c, and 3d show in cross-section various configurations and stages of use of one pocket containing the disinfecting solution.

The porous external layer 220 may be made from a flexible material selected to contain the disinfecting solution 250 inside the pocket 200 unless pressurized. The pores of the external layer 220 may be located throughout a portion thereof or throughout its entire external surface area. The size of the pores may be selected depending on the viscosity of the disinfecting solution and the pressure that may be applied thereto. Importantly, the combination of the disinfecting solution viscosity and the pore sizes may be selected to assure that (i) the disinfecting solution 250 is contained inside the pocket 200 when not pressurized, and (ii) the disinfecting solution 250 is able to flow across the pores and onto the external surface of the protective garment 100 when pressurized. Less viscous solutions would necessitate smaller size pores so as to contain the disinfecting solution inside the pocket 200 prior to applying pressure thereto. In embodiments, a "puree-like" consistency of the disinfecting solution 250 may be used so as to reliably retain the disinfecting solution 250 inside the pocket 200. A pore size ranging from about 1/64 mm to about 1 mm may be selected in that case for the suitable external porous layer 220.

To further improve the ability of the protective garment to contain the disinfecting solution inside the pocket 200 prior to use, a removable external impermeable protective layer may be provided (not shown) and configured to seal the external porous layer 220 until removed therefrom. Removal of the external protective layer may expose the external porous layer and allow the disinfecting solution to flow towards the external surface of the protective garment when pressurized.

The extent of the pressurization of the disinfecting solution may be selected to not exceed about 200 mmHg. In embodiments, the extent of pressurization sufficient to cause the disinfecting solution 250 to flow across the pores of the flexible external porous layer 220 may be selected to be about 20 mmHg, about 50 mmHg, about 75 mmHg, about 100 mmHg, about 150 mmHg, about 200 mmHg or any other suitable pressure as the present invention is not limited in this regard.

Depending on the selection of the suitable disinfecting solution, its viscosity may be adjusted to make it useful for the purposes of the present invention. A suitable thickener or thinner may be added to achieve the desired viscosity but without compromising the ability to disinfect the protective garment of the invention. When not pressurized, the disinfecting solution 250 may be retained inside the flexible chamber 210 as its viscosity and surface tension do not allow it to substantially flow through the pores of the external layer 220.

Applying external pressure to a pocket 200 shown in FIG. 3a may be achieved simply by rubbing a hand over the external surface of the protective garment. Various other methods of applying pressure may also be used such as manual compression or mechanical compression as described below.

In other embodiments of the invention, the disinfecting solution may be supplied inside a plurality of breakable capsules or microcapsules. The size of such capsules may range from about ⅛ mm to about 5 mm. The external membrane of such capsules may be made from a material that would be causes to rupture upon applying external pressure and lead to flowing of the disinfecting solution 250 to the external surface of the protective garment 100.

In yet other embodiments, the disinfecting solution 250 may be supplied in breakable pouches configured to rupture and release the disinfecting solution 250 when inside the pocket 200. The pouch may be ruptured when external compression is applied thereto, for example when an internal capsule is broken causing the pouch to be cut. In alternative embodiments, a pull-on tab may be provided to cause the pouch to rupture once sealed inside the pocket 200.

Figure 3B:
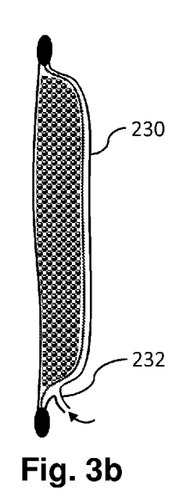

In further embodiments, pressurization of the flexible chamber 210 may be achieved by applying compression from an inflatable chamber 230 located inside or in close contact with the flexible chamber 210 such as behind thereof as seen in FIG. 3b, such inflatable chamber 230 may be inflated using pressurized fluid or gas supplied through a port 232.

Figure 3C:
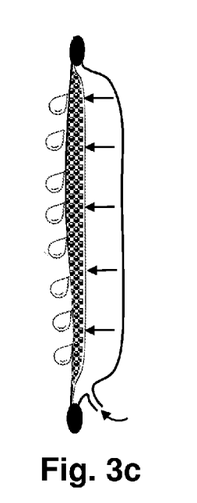
Figure 3D:
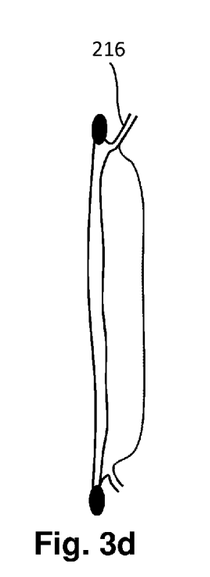

FIG. 3b shows an initial state of the pocket 200 in which the flexible impermeable chamber 210 is fully filled with disinfecting solution 250. FIG. 3c shows a state when the inflatable chamber 230 is at least partially expanded when filled with compressed gas such as pressurized air causing the inflatable chamber to inflate. Inflation of the inflatable chamber 230 in turn causes the membrane of the flexible chamber 210 to move towards the external layer 220 (in the direction to the left as seen in the illustration) causing pressurization of the disinfecting solution 250. Pressure increase of the disinfecting solution 250 in turn causes it to flow through the pores of the external layer 220 and emerge as drops on the external layer of the protective garment 100.

In embodiments, the volume of the pocket 200 may be selected to allow sufficient amount of the disinfecting solution to emerge on the surface of the protective garment 100 to disinfect thereof—once or several times. In some embodiments, the pockets 200 may be prefilled with disinfecting solution 250 prior to using the protective garment 100. In other embodiments, the flexible chamber 210 may be equipped with a filling port 216 configured to allow filling of the flexible chamber 210 with the disinfecting solution 250. The filling port 216 may be equipped with a check valve (not shown) to prevent the disinfecting solution 250 from flowing backwards through the filling port 216 once external pressure is applied to the flexible chamber 210.

While in some embodiments, filling of the flexible chambers 210 may be conducted well before or just prior to use of the garment 100, in other embodiments, such filling may be conducted after donning the protective garment 100. In further embodiments, such filling and refilling of the flexible chambers 210 may be conducted once or several times prior to, during, and after use of the protective garment 100 but prior to its removal. Depending on the nature of the disinfecting solution, the step of filling of the pockets 200 with this solution just prior or during use may be advantageous so as to assure that fresh disinfecting solution is utilized when the protective garment 100 is in use.

Figure 4:
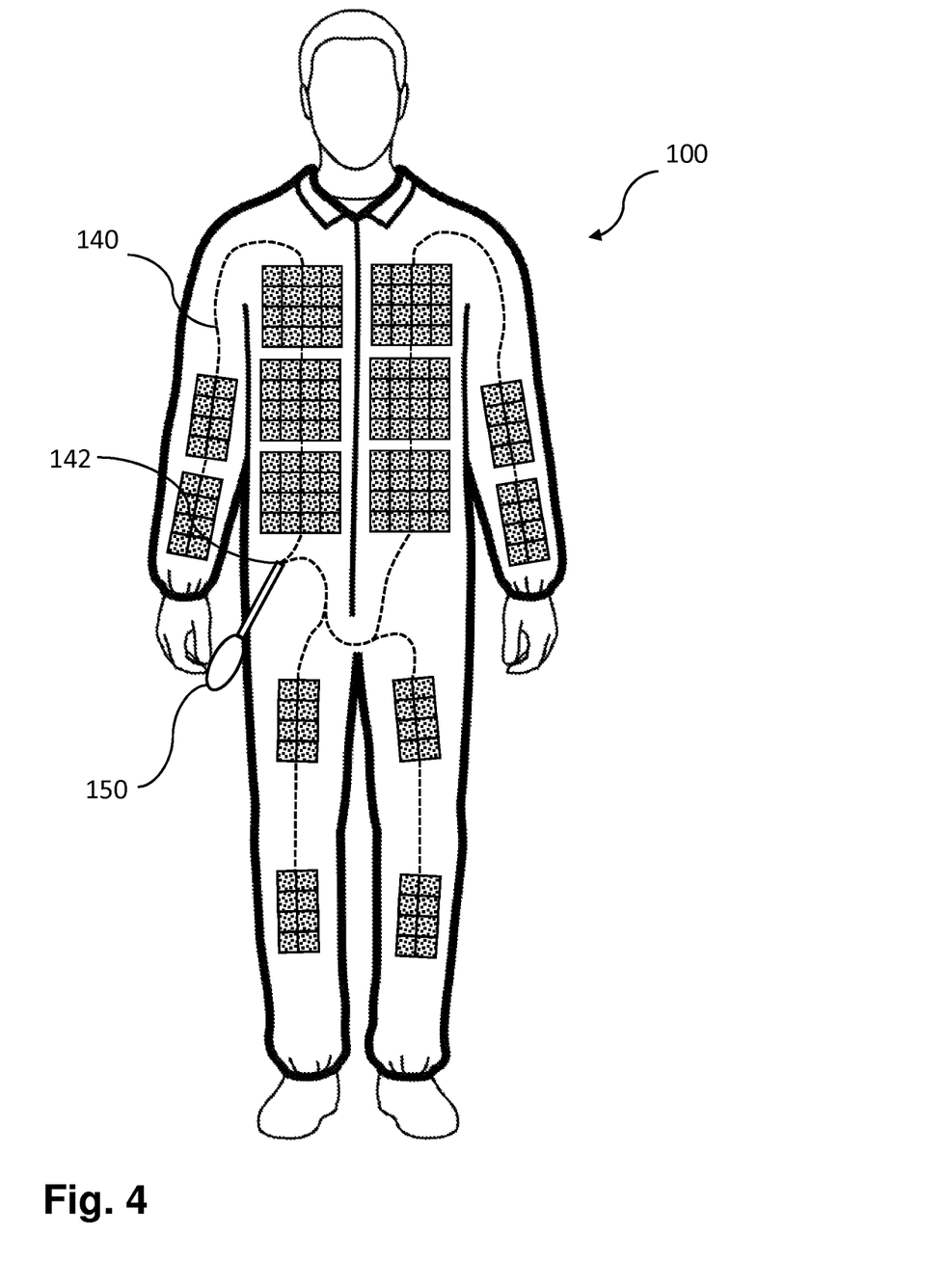
FIG. 4 shows the protective garment with manually-activated air pump fluidly connected to inflatable chambers.

FIG. 4 illustrates a protective garment 100 equipped with a plurality of tubes 140 (showed in dashed lines) configured for operatively connecting clusters of pockets 200 together with each other and with a central inflation point 142 configured for inflating the inflatable chambers 230. Provisions may also be made to fluidly and operably connect inflatable chambers 230 within each cluster such that a single tube 140 may be used to inflate all inflatable chambers 230 at once within each pocket cluster or the entire protective garment.

Inflation of the inflatable chambers 230 may be made through a single central inflation point 142 using a manual compressible bulb 150 as seen in FIG. 4. In other embodiments, an automatic inflator 160 may be positioned somewhere on the protective garment 100 and operably connected to the inflation point 142. The automatic inflator 160 may be positioned for example in an internal pocket of the protective garment 100—see FIG. 5, so as to prevent its exposure to the external pathogens. The automatic inflator 160 may be equipped with a single START button 162, which can be activated by pressing through the garment 100. In embodiments, the automatic inflator 160 may be made reusable and configured to attach to a disposable central inflation point 142 prior to using the protective garment 100 via a suitable connector fitting. After using and removal of the protective garment 100, the automatic inflator 160 may be retrieved, disconnected, optionally recharged and then used again with another protective garment. In other embodiments, the automatic inflator 160 may be permanently built into the protective garment 160 and designed for a single use. In this case, the protective garment may be discarded together with the automatic inflator 160 after its use is complete.

Figure 5:
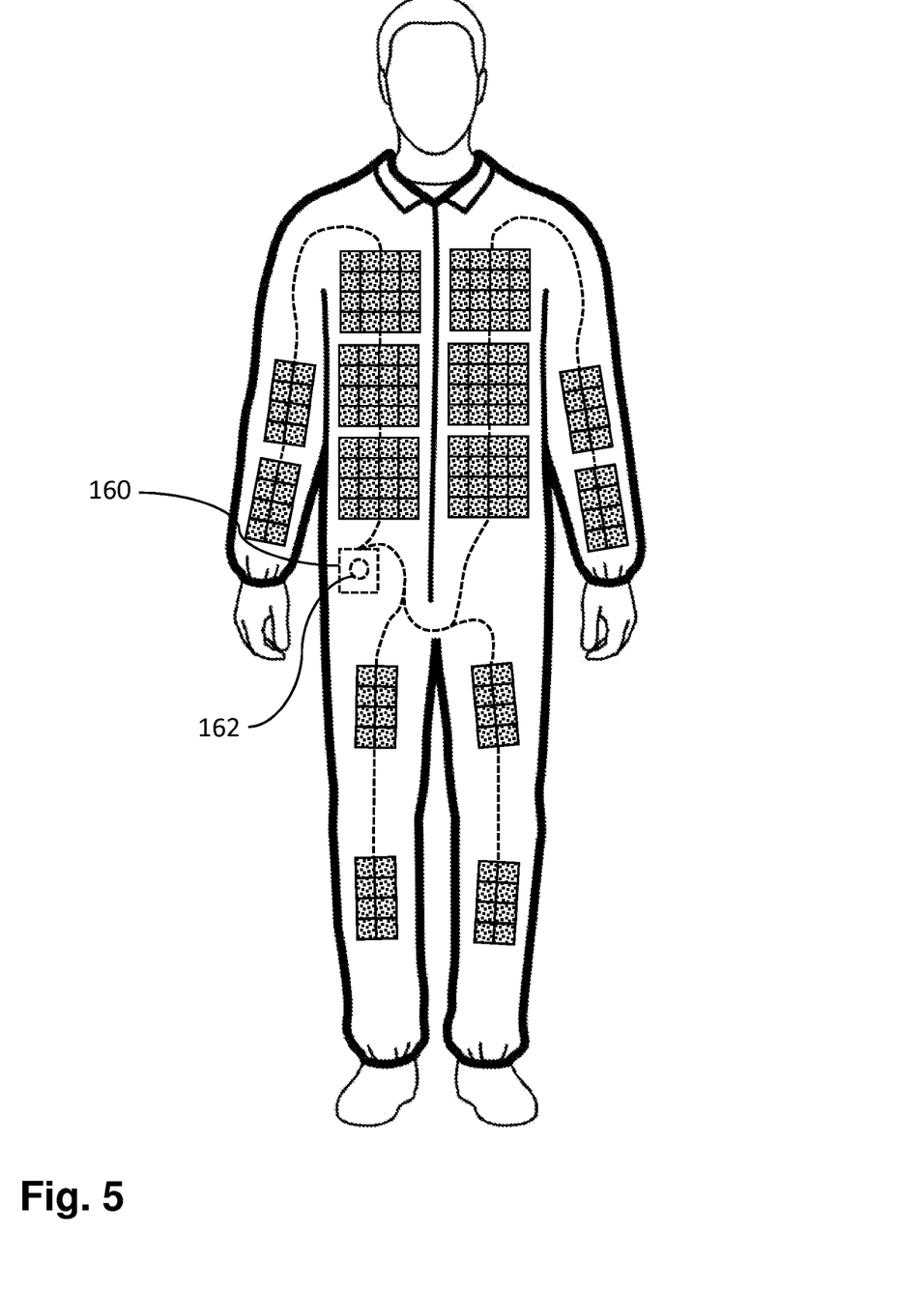
FIG. 5 shows the same except for use of an automated inflator in place of the manually-activated air pump.

The automatic inflator 160 may be configured to cause inflation of the inflatable chambers 230 once or every time the START button is pressed. In other embodiments, the automatic inflator 160 may be activated on demand, once or on a periodic predetermined schedule, for example every 30-45 min. The automatic inflator 160 may include a battery, a small air pump, a controller based on a computer processor and a START button. Other components of the automatic inflator 160 may include one or more pressure sensors and valves configured to monitor and control the process of inflation. In other embodiments, the automatic inflator 160 may contain a small canister with pressurized gas. In this case, the automatic inflator 160 may include suitable valves and pressure sensors configured to allow at least some gas (such as compressed air) to flow under pressure through the central inflation point 142 to cause inflation of the inflatable chambers 230.

Figure 6:
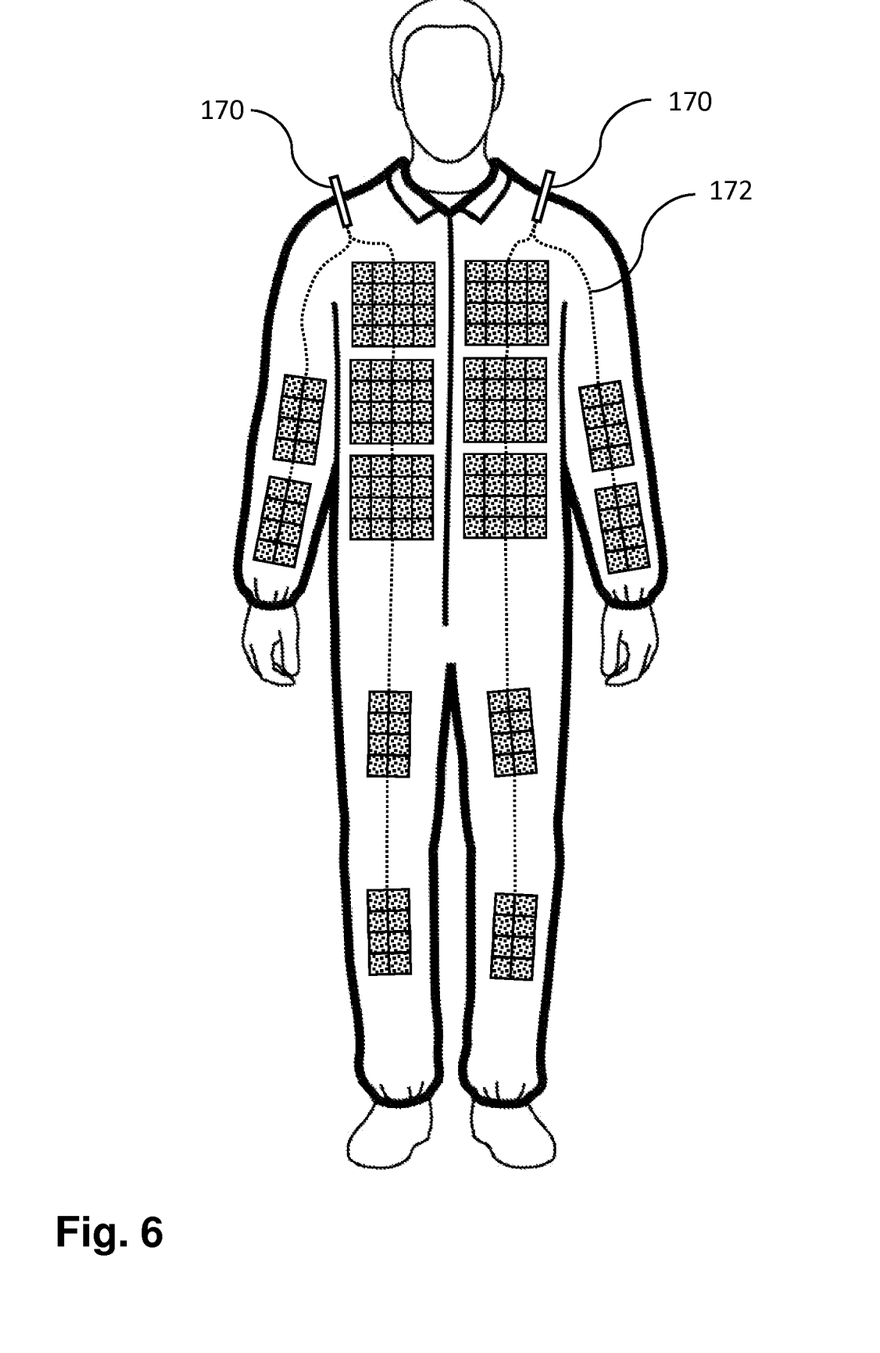
FIG. 6 shows the protective garment equipped with a filling port fluidly connected to all flexible chambers so as to allow filling and/or replenishment of pockets with the disinfecting solution.

FIG. 6 illustrates the protective garment 100 of the present invention equipped with a system of filling tubes 172 (shown in dotted lines) fluidly connected with the filling ports 216 of the flexible chambers 210. These filling tubes 172 may be built into or incorporated with the fabric of the protective garment 100 or alternatively routed along its internal or external surface. In embodiments, the system of filling tubes 172 may be configured to facilitate filling of individual pockets 200 or pocket clusters with the disinfecting solution 250. In some embodiments, additional fluid connections may be provided within each pocket cluster to direct disinfecting solution from the filling tubes 172 to each flexible chamber 210.

Filling tubes 172 may be equipped with one or more filling ports 170 configured to fill or replenish the flexible chambers 210 with the disinfecting solution 250. Appropriate quick-connect couplings and flow stopping valves may be provided as part of each filling port 170 to allow their opening, connecting to the source of disinfecting solution 250, filling the protective garment therewith and closing off the filling ports 170. In some embodiments, one or more filling ports 170 may be positioned on the upper portion of the protective garment 100 so as to facilitate the disinfecting solution 250 to flow down towards the pockets 200 by gravity. Advantageously, the presence of the external porous layer 220 eliminates the need to pull vacuum or evacuate air prior to filling the pockets with the disinfecting solution 250—the air will naturally escape through the pores of the external layer 220 as the pocket 200 is being filled with the disinfecting solution 250.

One further advantage of providing a filling port 170 is that the choice of the disinfecting solution may be made at the last minute—so as to keep it fresh and/or adjust the choice of the disinfecting solution based on the particular pathogen or another environmental threat if that is not known in advance.

In further embodiments, a pressurized source of disinfecting solution may be provided and configured to connect to the filling port 170 with a suitable quick-connect coupling. This configuration of the protective garment 100 features the ability for the user to wear the garment 100 with the pockets 200 being flat, collapsed and empty, at least at the beginning of its use—making the protective garment 100 operable with less weight. Sometime during or after use of the protective garment 100 is complete, the user may connect the pressurized source of the disinfecting solution to the protective garment 100 and cause the disinfecting solution 250 to flow towards the pockets 200. Continuous supply of pressurized disinfecting solution will cause it to flow through the pores of the flexible external layer 220 and onto the external surface of the protective garment 100, whereby disinfecting thereof. The protective garment 100 may then be safely removed and discarded. This embodiment has an additional advantage of providing the external porous layer throughout a substantial area or the entire surface of the protective garment, as there is little or no concern about the increased weight of the garment due to all the disinfecting solution contained therein. Such disinfected solution may be forcefully infused just at the right time prior to removal of the protective garment.

A variety of disinfecting solutions may be suitable for the purposes of the present invention depending on the nature of the pathogen or another environmental threat. In case of the Ebola virus, a chlorine bleach solution may be used as well as a variety of other commercially available and approved solutions. Other substances that may be used alone or in combination as a disinfecting solution 250 may include a hydrogen peroxide, an alcohol, a peracetic acid, a formaldehyde, a glutaraldehyde, an ortho-phthalaldehyde, an iodophor, a phenolic, and a quaternary ammonium compound.

In addition to a core disinfected compound (optionally adjusted to achieve proper viscosity with a thickener or a thinner additive), the disinfecting solution 250 may further include an additive with a coloring agent, which may be selected to have a color in contrast with the color of the external surface of the protective garment 100. This may be advantageous so as to easily assure that the external surface of the garment 100 is fully covered with the disinfecting solution 250. Examples of pair of contrast color may include providing the protective garment in white or yellow, while providing the coloring agent in green or blue. The choice of the coloring agent may be selected to not compromise the ability of the disinfecting solution 250 to eradicate the pathogen on contact. One example of a suitable coloring agent may be an inert food coloring.

A further improvement to the disinfecting solution 250 may be an optional addition of an additive with an evaporating agent selected to increase a rate of drying of the disinfecting solution 250 once on the external surface of the protective garment 100. Rapid evaporation of the disinfecting solution 250 off the surface of the protective garment may be used to cause active cooling of the external surface of the protective garment 100. Reducing the temperature of the protective garment 100 may be especially beneficial when the protective garment is used in hot ambient environment such as a field hospital in Africa. Cooling the protective garment 100 may improve the comfort of the user while wearing thereof. Examples of suitable evaporating agents include alcohol, water, various organic and inorganic solvents.

Inflation of an inflatable chamber inside or next to the flexible impermeable chamber 210 containing the disinfecting solution 250 may cause a change in the shape of the cross-section of the flexible chamber 210 from essentially flat to become more oval and ultimately round upon full inflation. That may have an undesirable effect of foreshortening the external surface of the overall fabric of the protective garment 100 and simultaneous bulging of the pockets 200. To minimize this effect, the protective garment 100 of the present invention may be equipped with a backing layer placed along the inside surface thereof. Such backing layer may be placed behind the flexible chambers 210 so as to position the flexible chambers 210 and the inflatable chambers between itself and the external surface of the garment. The backing layer may be made more rigid (less flexible) than the garment fabric itself. Inflation of the inflatable chamber in that case will cause its predominant expansion in a direction towards the flexible porous external layer, whereby limiting foreshortening of the external surface of the garment.

Figure 7:
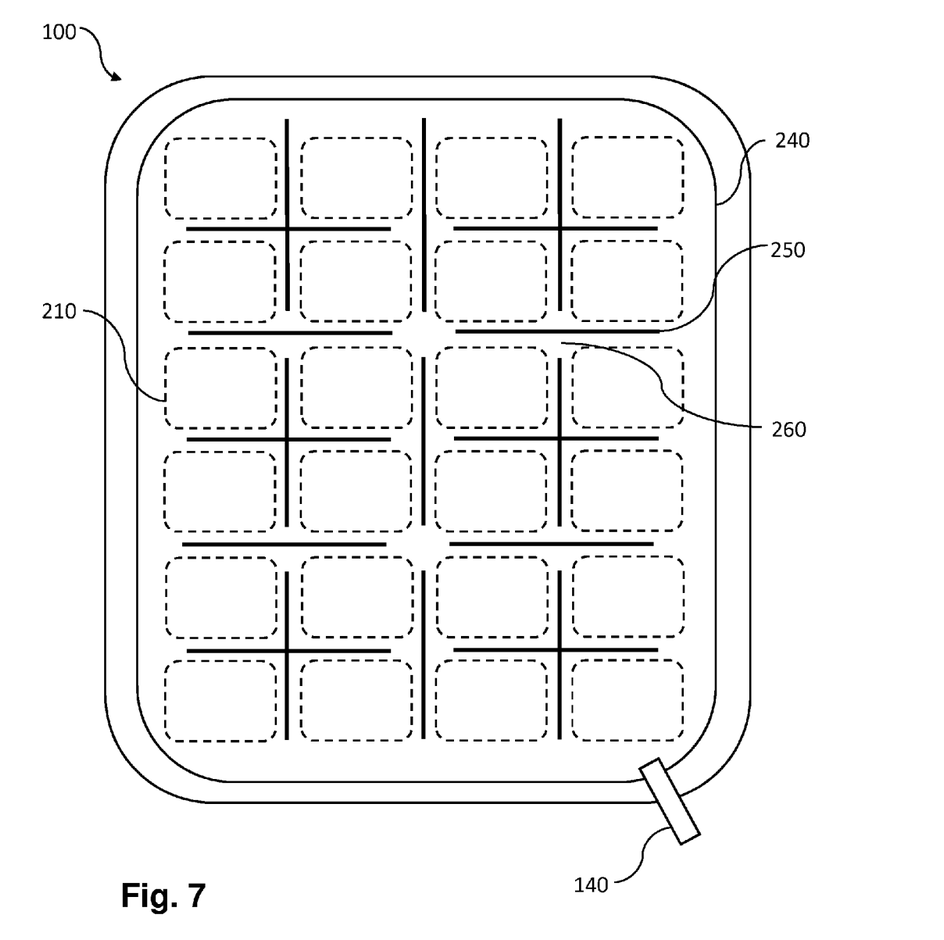
FIG. 7 shows a view from the inside of the garment illustrating one useful configuration of the pockets and a backing layer.

FIG. 7 illustrates a view from the inside of the protective garment 100 in one example of such arrangement. A larger backing layer 240 is seen placed over the inside surface of the garment 100 and sealed thereto along its peripheral edge, whereby forming a single inflatable chamber inbetween itself and the external surface of the garment 100. Incorporated with the external surface of the garment 100 are one or more flexible chambers 210 located under the backing layer 240 and shown in FIG. 7 in dashed lines. Inflation of the space between the backing layer 240 and the fabric of the protective garment 100 may be conducted through an inflation port 140, operably connected to a source of pressurized gas elsewhere in the protective garment 100.

In use, injection of the compressed air through the inflation port 140 may cause applying external compression to the flexible chambers 210 therefore causing the disinfecting solution to emerge on the external surface of the protective garment.

To minimize foreshortening of the garment fabric 100, the backing layer 240 in addition (or as an alternative) to being more rigid than the garment fabric 100, may be attached to the fabric 100 not only along its peripheral edge, but also at least partially along the areas between the spaced apart flexible chambers 210.

Various techniques of attaching one or more layers of the protective garment 100 to each other may be used in production thereof. Examples of suitable attachment techniques may include gluing, stitching, welding, heat sealing, crimping, stapling, laser sealing, etc. In addition to providing a fluid-tight seal, such techniques may be selected to assure suitable flexibility of the assembly so as not to impede onto the movement freedom of the user while wearing the garment of the present invention.

Attachment of the backing layer 240 to the fabric 100 may be done along the lines 250 between the flexible chambers 210—such lines 250 may have interruptions 260 to allow pressurized gas (such as compressed air) to penetrate everywhere throughout the area of the backing layer 240 using a single inflation port 140. In embodiments, attachment lines 250 may be selected to go along a portion of a single flexible chamber or along several spaced apart flexible chambers. In other embodiments, the backing layer 240 may be attached to the fabric 100 at one or a plurality of attachment dots, such dots located throughout the area of the backing layer 240 at areas between the spaced apart flexible chambers 210.

The stiffness of the backing layer 240 may be selected to be at least twice higher than that of the fabric 100. On the other hand, making the backing layer 240 too rigid while covering a large portion of the protective garment 100 is not desirable as it may restrict the motion of the user inside the garment. To address this concern, some embodiments of the protective garment 100 may feature the backing layer 240 divided into sections, each section may be configured to flex relative to another section—for example along the flexing living hinges that may be formed using the attachment lines 250.

While FIG. 7 shows the backing layer 240 forming an integral portion of the inflatable chamber, in other embodiments, such inflatable chambers may be made separately from a suitable flexible polymer material such as polyethylene, polyurethane or alike. In further embodiments, such inflatable chambers may be made to be integral with the flexible chambers 210, while in yet other embodiments, all elements of the protective garment may be made separately and attached together to form several successive layers of protective garment: the external fabric 100; the external porous layer; the internal flexible chamber with the disinfecting solution, the inflatable chamber; and finally the backing layer 240—as the invention is not limited in this regard.

In addition to a full protective garment with a self-disinfecting feature as described above, the present invention describes a conversion kit allowing to add a self-disinfecting feature to a conventional personal protective garment. Such conversion kit may include a plurality of pockets, each pocket comprising a flexible impermeable chamber covered by and sealed along an edge with a flexible porous external layer. The flexible chamber in turn may contain the disinfecting solution or be configured to be filled with the disinfecting solution. The flexible chamber may be further configured in such a way that compression thereof may cause pressurization of the disinfecting solution, which in turn may force this disinfecting solution to flow from the pocket across and through the porous external layer and spread over the external surface of the personal protective garment so as to disinfect thereof.

Figure 8:
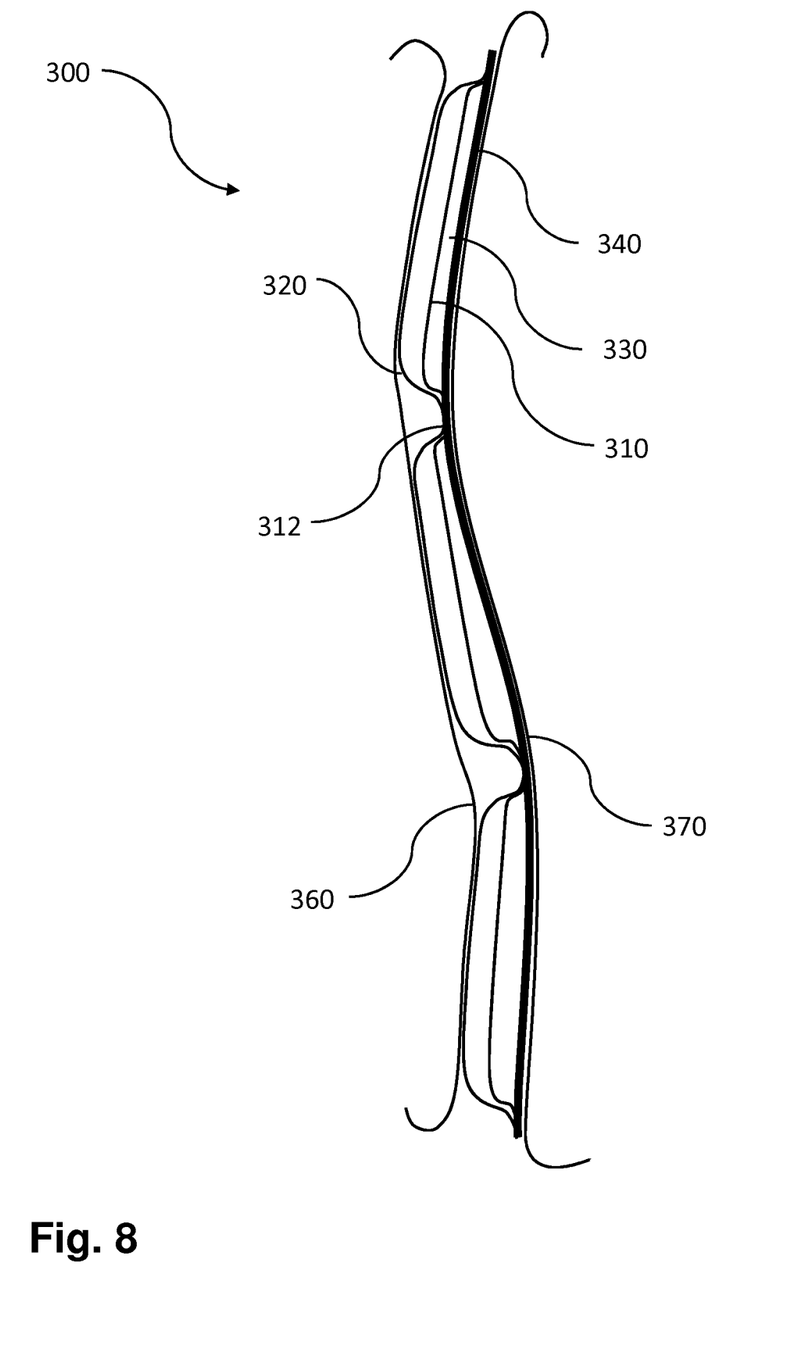
FIG. 8 shows a cross-sectional view of the pockets of the conversion kit, the pockets are equipped with outside and inside removable protective layers.

One example of a conversion kit 300 is illustrated in FIG. 8 and includes a backing layer 340 forming an inflatable chamber 330 between itself and the flexible membrane 310. The membrane 310 in turn forms a flexible chamber with the external porous layer 320, all three elements may be attached together and sealed along the seals 312. As described above, the backing layer 340 may be made less flexible than other elements of the conversion kit 300 so as to cause preferential expansion of the inflatable chamber towards the flexible chamber and cause the disinfecting solution located inside the flexible chamber to flow through the pores of the external porous layer 320 towards the external surface of the conversion kit (on the left side of the drawing in FIG. 7).

Other design elements as described above may also be incorporated in the conversion kit such as various shapes and relative positions of the pockets, a variety of filling ports, variety of disinfecting solutions and solution additives, use of compressed air, etc.

To attach the conversion kit 300 to a personal protective garment, an adhesive layer may be provided on the surface of the backing layer 340 facing the garment. Such adhesive layer may be covered with a first removable protective layer 370. In embodiments without the inflatable chamber, the adhesive layer (and the first removable protective layer 370) may be applied to the outside surface of the flexible chamber 310, which in that case will face the external surface of the personal protective garment.

In use, the conversion kit 300 may include one or more pockets containing the disinfecting solution or configured to be filled with or to be replenished with the disinfecting solution. The protective layer 370 may be removed and the pockets may be placed on top of the personal protective garment over its external surface. Positioning of the pockets may be conducted over the entire area of the personal protective garment or over the areas of most importance such as those described above.

In addition to the first removable protective layer 370 cover the adhesive layer suitable for attachment of the pockets onto the protective garment, a second removable protective layer 360 may be provided on the other side of the pockets of the conversion kit 300—to cover the porous external layer 320 and prevent premature leakage of the disinfecting solution from the pockets during storage and prior to use. Once the pockets are positioned on the personal protective garment, the second removable layer 360 may be removed prior to or during the use of the protective garment—and before its removal by the user.

In addition to using the protective garment by healthcare workers when treating patients with Ebola virus or other highly contagious infections, the protective garment of the invention may be used in the clean-up or aftermath of a nuclear, radiological, chemical or biological attack including a terrorist attack with a "dirty bomb"—in order to neutralize the harmful environment and protect the hazmat crew. In that case, appropriate solution may be selected depending on the nature of the contaminated environment.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the appended claims.

What is claimed is:

1. A self-disinfecting protective suit comprising: arm sleeve, leg, and chest areas configured to cover a wearer, a plurality of pocket clusters located on predetermined areas of the suit, wherein each pocket cluster comprises a plurality of individual pockets, each individual pocket comprising a flexible impermeable chamber covered by and sealed along an outer peripheral edge with a flexible porous external layer forming an internal volume, said flexible porous external layer being a part of an external surface of said protective suit, said internal volume of each pocket containing a disinfecting solution, a plurality of inflatable chambers throughout the protective suit, wherein each of said individual pockets further comprises one of said plurality of inflatable chambers positioned behind said flexible impermeable chamber, said plurality of inflatable chambers are configured to cause pressurization of said disinfecting solution when the plurality of inflatable chambers are at least partially inflated, a rigid backing layer attached and sealed along its peripheral edge along an inside surface of said protective suit, the rigid backing layer positioned behind the flexible impermeable chamber of each of said individual pockets, wherein said inflatable chambers predominantly expand in a direction towards said flexible porous external layer, wherein said rigid backing layer is configured to limit foreshortening of said external surface of said protective suit when the inflatable chambers are inflated, and wherein inflation causes compression of said flexible impermeable chambers and said disinfecting solution is urged to flow from said internal volume through the porous external layer and spread over said predetermined areas of said external surface of said protective suit so as to disinfect thereof.

2. The protective suit as in claim 1, wherein said flexible porous external layer is configured to contain said disinfecting solution inside said individual pocket unless compressed.

3. The protective suit as in claim 2, wherein said disinfecting solution is characterized by a solution viscosity, said flexible porous external layer is characterized by a range of pore sizes, wherein said protective suit is characterized by a predefined combination of said solution viscosity and said range of pore sizes selected to contain said disinfecting solution inside said flexible impermeable chamber unless said disinfecting solution is pressurized.

4. The protective suit as in claim 1, wherein said plurality of inflatable chambers are fluidly connected to a pump or a source of compressed gas, wherein activation of said pump or said source of compressed gas causes at least a partial inflation of said plurality of inflatable chambers.

5. The protective suit as in claim 4, wherein said pump is configured to be manually operated so as to cause said disinfecting solution to flow to the external surface of said protective suit on demand.

6. The protective suit as in claim 1, wherein said disinfecting solution comprises an additive with a coloring agent.

7. The protective suit as in claim 6, wherein said coloring agent is characterized by a color selected to contrast against a color of said external surface of said protective suit, whereas when flowing outside said pocket clusters, said disinfecting solution is visible over said external surface of said protective suit so as to allow determination of whether a desired area of said protective suit is sufficiently covered with said disinfecting solution.

8. The protective suit as in claim 1, wherein said disinfecting solution comprises an additive with an evaporating agent so as to increase evaporation of said disinfecting solution off the external surface of said protective suit, whereby causing active cooling thereof.

9. The protective suit as in claim 1, wherein said disinfecting solution is selected from a group consisting of a chlorine bleach solution, a hydrogen peroxide, an alcohol, a peracetic acid, a formaldehyde, a glutaraldehyde, an ortho-phthalaldehyde, an iodophor, a phenolic, a quaternary ammonium compound, or a combination thereof.

10. The protective suit as in claim 1, further comprising a removable external protective layer configured to seal said external porous layer and contain said disinfecting solution inside said plurality of pocket clusters while storing said protective suit prior to use, wherein removal of said external protective layer exposes each porous external layer of said plurality of pocket clusters and allows the disinfecting solution to flow out when pressurized.

11. The protective suit as in claim 1, further comprising a filling port fluidly connected to each flexible impermeable chamber of said plurality of pocket clusters, said filling port is configured to allow filling or replenishing of said flexible impermeable chambers with said disinfecting solution prior to, during or after use, wherein the weight and size of said protective suit when stored or used with said flexible impermeable chambers being dry, collapsed and empty is minimized.

12. The protective suit as in claim 11 further comprising a source of pressurized disinfecting solution configured to be attached to said filling port, wherein said protective suit can be disinfected by attaching said source of disinfecting solution and causing said disinfecting solution to flow towards said pocket clusters, through said porous external layer and spreading over at least a portion of the external surface of said protective suit.

* * * * *